(12) United States Patent
Redford

(10) Patent No.: US 8,409,852 B2
(45) Date of Patent: Apr. 2, 2013

(54) AQUATIC-BASED MICROALGAE PRODUCTION APPARATUS

(76) Inventor: Daniel S. Redford, San Dimas, CA (US)

( * ) Notice: Subject to any disclaimer, the term of this patent is extended or adjusted under 35 U.S.C. 154(b) by 0 days.

(21) Appl. No.: 13/473,886

(22) Filed: May 17, 2012

(65) Prior Publication Data

US 2012/0329147 A1 Dec. 27, 2012

Related U.S. Application Data

(60) Provisional application No. 61/571,107, filed on Jun. 21, 2011.

(51) Int. Cl.
*C12M 1/00* (2006.01)
*A01G 7/00* (2006.01)
(52) U.S. Cl. ............... 435/292.1; 435/257.1; 47/1.4
(58) Field of Classification Search ............... 435/292.1; 47/1.4
See application file for complete search history.

(56) References Cited

U.S. PATENT DOCUMENTS

| | | | |
|---|---|---|---|
| 3,955,317 A | 5/1976 | Gudin | |
| 4,043,903 A | 8/1977 | Dor | |
| 4,888,912 A | 12/1989 | Murray | |
| 6,786,002 B2 | 9/2004 | Prescott | |
| 7,921,595 B1 | 4/2011 | Monson et al. | |
| 7,980,024 B2 | 7/2011 | Berzin | |
| 8,092,679 B1 | 1/2012 | Jensen et al. | |
| 8,110,395 B2 | 2/2012 | Lewnard et al. | |
| 8,161,679 B2 * | 4/2012 | Albus et al. | 47/1.4 |
| 2006/0148071 A1 | 7/2006 | Bauer et al. | |
| 2008/0181999 A1 | 7/2008 | Yang | |
| 2009/0130706 A1 * | 5/2009 | Berzin et al. | 435/41 |
| 2009/0181434 A1 * | 7/2009 | Aikens et al. | 435/105 |
| 2010/0216203 A1 | 8/2010 | Trent et al. | |
| 2011/0283608 A1 * | 11/2011 | Patel et al. | 47/1.4 |

FOREIGN PATENT DOCUMENTS

| | | | |
|---|---|---|---|
| JP | 53139357 A | * | 12/1978 |
| WO | WO 2008134010 | | 11/2008 |
| WO | WO 2010117726 A1 | * | 10/2010 |

* cited by examiner

*Primary Examiner* — William H Beisner
(74) *Attorney, Agent, or Firm* — Monty Simmons; Simmons Patents

(57) ABSTRACT

An aquatic-based algae production apparatus employing a microalgae production support assembly (30) and a cluster of six floating, closed loop, flatbed, $CO_2/O_2$ gas-permeable, photo-bioreactors, offering an economical solution for microalgae industrial production. The apparatus's bioreactors are submerged in the proximity of the water surface mark (20) for maximum light exposure and for $CO_2/O_2$ continue diffusion. A microalgae processing and control assembly (200) is monitoring the algae growth for each photo-bioreactor in the cluster, and is cyclically harvesting the microalgae. After harvesting the microalgae are transferred into a submerged variable-volume microalgae storage tank (250). Solar photovoltaic panels (400) and (500) are supplying the energy required for the operation of the apparatus. Swivel electrical propellers (330) attached to the bottom of the apparatus protective outer barrier (300) are controlling the apparatus's water deployment.

20 Claims, 4 Drawing Sheets

US 8,409,852 B2

AQUATIC-BASED MICROALGAE PRODUCTION APPARATUS

CLAIM TO PRIORITY

This application claims priority to U.S. Provisional Patent Application No. 61/571,107 filed on Jun. 21, 2011 under the name Aquatic-based Algae Production Apparatus and is hereby incorporated by this reference for all purposes and for all that it discloses.

TECHNICAL FIELD

The invention relates to the fields of engineering, gas-permeable closed photo-bioreactors, and fluid dynamics. The invention provides for an energy-neutral, autonomic, aquatic-based microalgae production apparatus for the continued daily growth, in situ separation and storage of microalgae cultures.

BACKGROUND

The production of alternative fuels, generically called bio-fuels, is currently dominated by the conversion of high cost feed substrates such as sugar cane, corn, rapeseed, palm oil and other terrestrial crops predominantly used as food for human/animal consumption. While the technology exists to convert these feed-stocks to bio-fuels, there is not sufficient arable land or fresh water resources to meet our society's enormous demand for energy.

The United States alone uses over 168 billion gallons of gasoline per year. The current U.S. output of bio-fuels, particularly ethanol made from corn, covers only 5 billion gallons per year and is representing just 3% of the gasoline used in the U.S. In addition, the ethanol from corn production has triggered a 50% increase in the market price of corn on global commodity markets.

The second most predominant alternate renewable energy source has been the conversion of cellulose based waste products to bio-fuels. The relative limited availability of biomass supply, its high cost of transportation to the processing facility, as well as the initial investments, has limited the scale of this technology to less than 0.06% of the U.S. needs.

The third and the most promising alternate renewable energy source is the use of photoautotrophic organisms, such as microalgae with high content of oil, to produce bio-fuels. The primary benefit of this technology is the combining of the process of the conversion of solar energy into cellular biochemical energy. Photoautotrophic organisms are those that can survive, grow and reproduce with energy derived entirely from the sun through the process of photosynthesis. Photosynthesis is essentially a carbon recycling process through which inorganic carbon dioxide is combined with solar energy, other nutrients and cellular biochemical processes to synthesize carbohydrates required to sustain growth. Photosynthesis occurs in plants, algae, and many species of bacteria.

Previous efforts for larger scale production have focused on growing photoautotrophic organisms in land-based open ponds or raceways that provide similar growing conditions found in nature. A major drawback of this approach is that growing conditions cannot be well controlled, resulting in uncertain production outputs, batch contaminations and other significant technical challenges to bring the micro-algae growing and harvesting technology to a commercial reality.

Below are the six most important reasons why the current land-based microalgae growth and harvesting system have failed to become a significant renewable energy source:

1. Water requirements. Microalgae need a lot of water—they grow in it. Water evaporation is a major detrimental factor.

2. Light requirements. Microalgae need a lot of light, and to receive it, they typically require a flat waterbed no deeper than four inches but with horizontal surface area of hundreds of square yards. That means a lot of perfectly flat land must be converted into waterbeds and filled with water in order to accommodate microalgae growth. The logistics addressing the construction of thousands of acres of flat waterbeds and the related water requirements are overwhelming and cost prohibitive. One of the main concerns related to the land allocation for building wide-scale flat waterbeds is the potential displacement of croplands currently used for food supply.

3. Water temperature factor. Microalgae growing season is largely dependent on location and, aside from tropical areas, is limited to the warmer months. Large day and night temperature variation specific for desert climate are extremely detrimental in microalgae growth.

4. Carbon dioxide requirements. Microalgae cannot use directly the atmospheric carbon dioxide. The carbon dioxide, crucial for algae production yield, must be dissolved in water. For stationary flat waterbeds the logistics and energy requirements to constantly provide microalgae culture with the needed carbon dioxide are cost prohibitive.

5. Contamination factor. Microalgae are very vulnerable for being contaminated by other microalgae species and bacteria. Most often the species of microalgae that have the highest oil content are not necessary the strongest and quickest to reproduce.

6. Energy factor. The current cost for over-land or on-shore lines for microalgae mass production, including fertilization, harvesting, transportation, and storage are extremely high and non-competitive with the existing fossil fuel economy.

One point of novelty of the present invention is that it economically addresses all the above-mentioned problems associated with land-based microalgae production systems while also being posed to facilitate a significant cost reduction in producing renewable energy source capable of competing with existing fossil fuel industry.

A search of the prior art did not reveal any patents that read on the instant invention. However, the following U.S. patent applications are considered related:

| U.S. patent application No. | Applicant(s) | Filed Date |
| --- | --- | --- |
| 8,161,679 | Albus et al. | Dec. 21, 2009 |
| 12/316,557 | Trent et al. | Dec. 5, 2008 |
| 7,980,024 | Berzin et al. | Apr. 25, 2008 |

Albus et al. teaches an open ocean floating algae farm built around a ship. The ship provides propulsion power for navigation, storage capacity for material and algae products, machinery for harvesting and processing the algae, housing for crew, and facilitate the maintenance of the floating farm. The invention also comprises transparent tubes that circulate a broth of seawater saturated with CO2, nutrients and algae. The circulation path flows from the ship through the tubes and back to the ship where the algae are filtered out ready to be processed. The transparent tubes circulating the algae broth are supported by a matrix of tubes filled with seawater that is neutrally buoyant and submerged just below the ocean surface.

Trent et al. teaches a method for producing hydrocarbons, including oil by processing algae and/or other microorganisms in an aquatic environment. This method employs flexible bags containing nutrient and seeds of algae growth. The bags having $CO_2/O_2$ exchange membranes are suspended at a controllable depth in an aquatic field. The algae are cultivated and harvested in the bags.

Berzin et al. teaches photo-bioreactor units flowing on a body of water such as a pond or a lake containing a liquid medium comprising at least one species of phototrophic organisms. The photo-bioreactor units are formed of flexible, deformable material and are configured to provide a substantially constant thickness of liquid medium. In certain embodiments a barrier between the photo-bioreactor units and the body of water upon which the unit is floating controls the heat transfer between the liquid medium and the body of water.

DISCLOSURE OF THE INVENTION

The general objective of the present invention is to offer an economically viable solution to all contemporary microalgae growth and harvesting related issues, by providing an energy-neutral, autonomic, aquatic-based large-scale microalgae production apparatus.

The present invention describes a microalgae production apparatus comprising a production support system and a microalgae producing system.

The apparatus production support system comprises a floating microalgae processing and control assembly surrounded by a floating support structure, shaped like a honeycomb, that is partitioning an aquatic field in a plurality of deployment areas defining six adjacent hexagons. A protective outer barrier structure shaped as a floating ring is encompassing the floating support structure.

The apparatus' microalgae producing system comprises a cluster of six hexagonal shaped flatbed photo-bioreactors having the dimensional characteristics of terrestrial flat waterbeds. They are positioned inside the honeycomb structure and around the centrally positioned microalgae processing and control assembly.

The apparatus' flatbed photo-bioreactors are deployed inside the cluster and are submerged in the proximity of the water surface to maximize light exposure, as well as carbon dioxide and oxygen transfer. The light exposed surface of each flatbed photo-bioreactor comprises a light transparent and CO2/O2 gas permeable membrane while a water exposed surface area comprises a CO2/O2 gas permeable membrane.

The CO2/O2 gas-permeable membranes allow the carbon dioxide dissolved in the surrounding water to enter the flatbed photo-bioreactors. Similarly, such membranes should also allow oxygen produced inside the photo-bioreactor to exit and diffuse into the surrounding water.

Each flatbed photo-bioreactor preferably comprises a dual-path water recirculation system to enhance algae growth and algae harvesting tasks. The algae-growth water recirculation path regulates the heat transfer between the water inside the flatbed photo-bioreactors and the surrounding water and helps maintain the photo-bioreactor's water temperature within predefined tolerances. The algae-harvesting water circulation paths are configured to harvest a predefined percentage/range (around 50%) of the algae present in the photo-bioreactor. Such a process defines at least part of a novel partial-harvest method.

Each photo-bioreactor in the cluster is in hydraulic communication with the centrally positioned microalgae processing and control assembly that constantly monitors the flatbed photo-bioreactor algae growth parameters including water temperature and nutrient levels and initiates and conducts partial harvesting. The partial harvesting method assures continue algae presence in the photo-bioreactors and gives flexibility in controlling their biological development. After harvesting, the algae are transferred into an underwater variable-volume storage tank attached at the bottom of microalgae processing and control assembly.

The algae production apparatus is designed to produce, store, and monitor all its electrical power needs. A plurality of solar photovoltaic panels are associated with the top of the microalgae processing and control assembly and on the apparatus' protective outer barrier structure shaped as a floating ring. The floating ring provides structural protection for the apparatus' flatbed photo-bio-reactors and hosts the electrical energy storage, navigation means such as electrical swivel propellers, as well as the anchoring and docking means.

A mast assembly positioned on top of the microalgae processing and control assembly is employed to anchor the apparatus' protective outer barrier structure and the floating protective structure to the microalgae processing and control assembly.

The mast also provides deployment for antennas, satellite dishes, and other electronic and visual identification means.

A motion facilitator controller located inside the watertight microalgae processing and control assembly, employs a global positioning system and several swivel electrical propellers attached to the bottom of the protective outer barrier structure to control the apparatus' water deployment coordinates and to initiate and control migration.

When required, a maintenance and logistic-support ship, which is preferably permanently in contact with the apparatus' motion facilitator controller, will dock the apparatus for maintenance purposes, to refresh its nutrients supply or to empty the content of the apparatus' microalgae storage tank when it approaches the designed capacity.

Consequently, embodiments of the disclosed invention address all six Micro-Algae' growth and harvesting related problems.

Problem No 1: Water Requirements.

The apparatus' photo-bioreactors are closed loop reactors floating submerged in the proximity of the water surface of any large body of water, oceans included; therefore, water evaporation related issues are minimal and perhaps eliminated.

Problem No 2: Light Requirements.

The apparatus employs a cluster or plurality of modular flatbed photo-bioreactors having a preferred height of only several inches with each said photo-bioreactor being covered by a flexible light-transparent membrane configured to allow sufficient light passage into the photo-bioreactors for algae growth.

Problem No 3: Water Temperature Factor.

The apparatus' flatbed photo-bioreactors are submerged, at least partially, in the proximity of the water surface. Additionally, the photo-bioreactor's algae growth recirculation path help control the heat transfer between the water inside the photo-bioreactor and the surrounding water. This allows the photo-bioreactor's water temperature to be maintained within predefined thresholds. Therefore, the large day and night temperature variations common to desert environments are eliminated or at least minimized.

Problem No 4: Carbon Dioxide Requirements.

Gas-permeable membranes cover the apparatus flatbed photo-bioreactors to allow large-scale surface diffusion for the carbon dioxide dissolved in the surrounding water. The Oxygen produced by the photo-bioreactor during operation is released back in the surrounding water using the same gas-permeable membranes. Therefore, the costs associated with carbon dioxide production and distribution is minimal to zero.

Problem No 5: Contamination Factor.

The apparatus employs closed loop flatbed photo-bioreactors can be operated far from land in deep non-nutritional waters with minimal airborne particulates that are known to cause algae contamination thereby minimizing or eliminating the risk of airborne algae contamination.

Problem No 6: Energy Factor.

A plurality of solar photovoltaic panels positioned on top of the fertilization and harvesting module and floating ring assembly supply all or substantially all of the energy required for the operation and control of the apparatus.

Thus, as described above, embodiments of the present invention minimize or eliminate: (a) the costs related to land based waterbed construction; (b) the displacement of croplands; and (c) a possible justification for food prices increases. Further, it is anticipated that a 50,000-litter Aquatic-based Microalgae Production apparatus having a 0.5 ha active photo-bio-reactive surface, and operating in 85 Degrees Fahrenheit waters, may reach a producing of microalgae equivalent to 100 barrels of green crude per day. A farm of 50 apparatus having a total of 25 ha of photo-bio-reactive surface may reach a production equivalent of 50,000 barrels of oil per day. Two hundred farms having a photo-bio-reactive surface of 5,000 ha may reach a production equivalent of 10 Million barrels of oil per day.

Additional objectives and embodiments of the present subject matter, not necessarily expressed in this summarized section, may include and incorporate various combinations of aspects of features or parts referenced in the summarized objectives above, and/or features or components as otherwise discussed in this application.

Other objects and advantages of the invention may be obvious from the description of the drawings, or may be learned through practice of the invention.

Those of ordinary skill in the art will better appreciate the features and aspects of such embodiments, and others, upon review of the remainder of the specification.

BRIEF DESCRIPTION OF THE DRAWINGS

A full and enabling description of the present subject matter, including the best mode thereof, directed to one of ordinary skill in the art, is set forth in the specification, which makes reference to the appended figures, in which:

FIG. 1b is a top view of the preferred embodiment depicted in FIG. 1a;

Figure 1B:
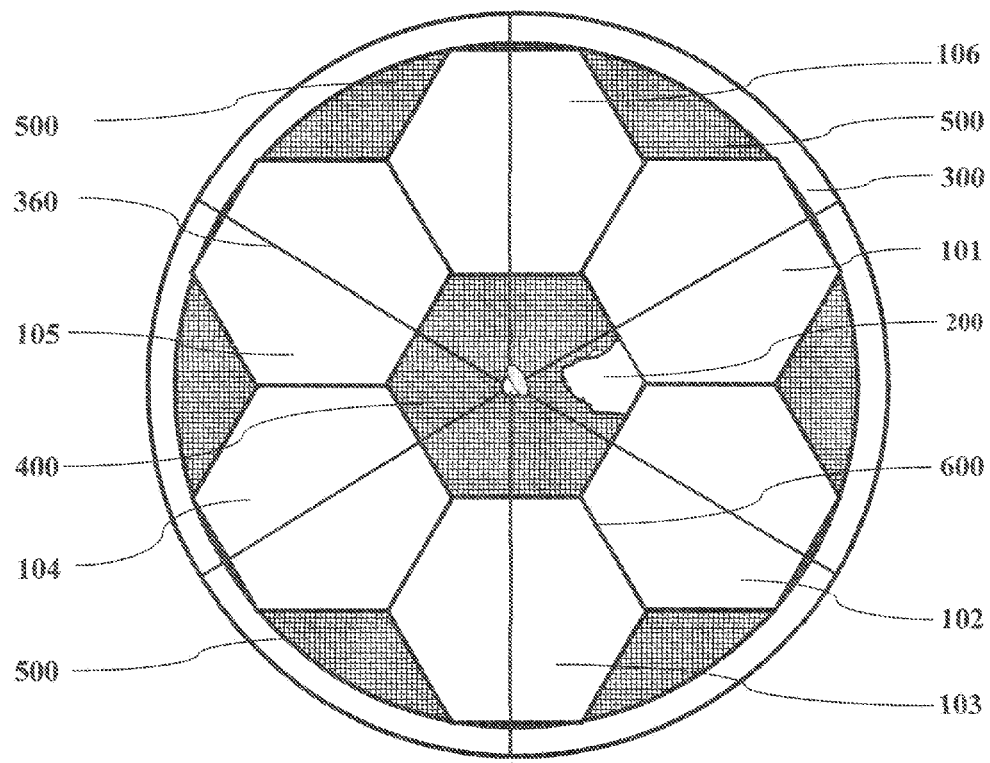

Repeat use of reference characters throughout the present specification and appended drawings is intended to represent the same or analogous features or elements of the present technology.

BEST MODE FOR CARRYING OUT THE INVENTION

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used on another embodiment to yield a still further embodiment. Thus, it is intended that the present invention covers such modifications and variations as come within the scope of the appended claims and their equivalents. Other objects, features, and aspects of the present invention are disclosed in or may be determined from the following detailed description. Repeat use of reference characters is intended to represent same or analogous features, elements or steps. It is to be understood by one of ordinary skill in the art that the present discussion is a description of exemplary embodiments only, and is not intended as limiting the broader aspects of the present invention.

DEFINITIONS

This section defines some of the terms used in this document while other terms are defined within the description.

For the purposes of this document, two or more physical items are "mechanically associated" (sometimes simply "associated") by bringing them together or into relationship with each other in any number of ways including a direct or indirect physical connection that may be releasable (snaps, rivets, screws, bolts, etc.) and/or movable (rotating, pivoting, oscillating, etc.) Similarly, two or more electrical items are "electrically associated" (sometimes simply "associated") by bringing them together or into relationship with each other in any number of ways including: (a) a direct, indirect or inductive communication connection, and (b) a direct/indirect or inductive power connection. Additionally, while a drawing may illustrate various electronic components of a system connected by a single line, it will be appreciated that such "signal line" may represent one or more signal paths, power connections/paths, electrical connections and/or cables as required by the embodiment of interest.

The term "photosynthetic organism", "phototrophic organism", or "biomass," includes all organisms capable of photosynthetic growth (including organisms modified artificially or by gene manipulation).

The phrases "transparent" and "at least partially transparent", when used in the context of a system component, a material, or a surface, refers to such system component, material, and/or surface allowing the penetration of a sufficient amount of light energy to enable photosynthesis within a phototrophic organism. Similarly, the term "RF Transparent" refers to a material or object that results in minimal reflection radiofrequency signals.

This document contains headers. Such headers are place markers inserted for the convenience of the reader and are not to be used in the construction of this document or to limit its meaning in any way.

DESCRIPTION

While the examples used in this document relate to flatbed, gas permeable, photo-bioreactors configured for the cultivation of algae, it will be appreciated that other photosynthetic organisms may be utilized in place of, and/or in addition to, algae.

A microalgae production apparatus according to one exemplary embodiment of the present invention is shown in FIG. 1a through FIG. 4.

Figure 1A:
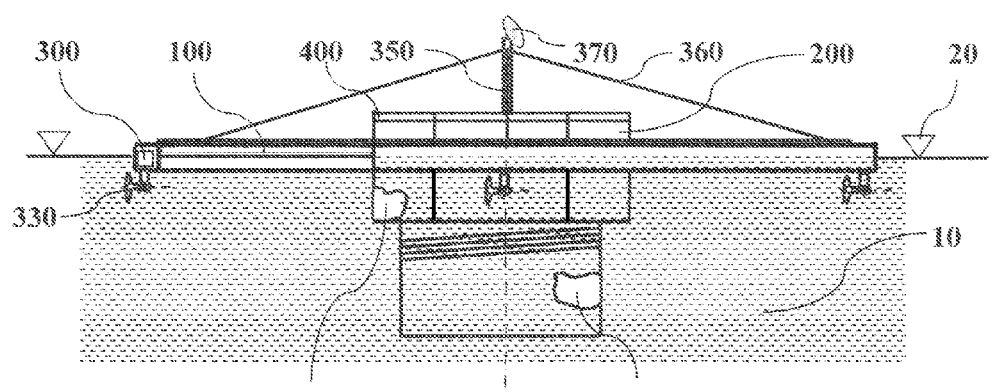
FIG. 1a is an elevation view with a partial cross section of a preferred embodiment of the invention floating partially submerged in an aquatic field.

FIG. 1a and FIG. 1b show a microalgae production support system (30) and a microalgae producing system (40), floating in an aquatic field (10) having an upper surface mark (20). The microalgae production support system (30) comprises a microalgae processing and control assembly (200) while the microalgae producing system (40) comprises a plurality of flatbed, gas-permeable, photo-bioreactor (101-106). As will be explained in more detail below, the flatbed, gas-permeable, photo-bioreactors (101-106) are in hydraulic communication with the microalgae processing and control assembly (200).

Microalgae Production Support System

FIG. 1b depicts the microalgae production support system (30) comprising a protective outer barrier structure (300) mechanically associated with a floating support structure (600), which surrounds the microalgae processing and control assembly (200). Protective outer barrier structure (300) encompasses the aquatic area defined by the area inside the outer perimeter of the floating support structure (600). Notably, the floating support structure (600) partitions such aquatic area in a plurality of deployment areas. Preferably, the floating support structure (600) is mechanically associated with both the protective outer barrier (300) and the microalgae processing and control assembly (200).

One suitable outer barrier (300) is a floating ring assembly. Additionally, one suitable floating support structure (600) is a floating-able honeycomb subassembly. Such floating-able honeycomb subassembly (600) is configured to mechanically associate the floating ring assembly (300) with the microalgae processing and control assembly (200). Such a honeycomb subassembly (600) configuration provides additional structural support to flat-bed photo-bio-reactors (100-106) as described in more detail below.

Preferably the outer perimeter of the support structure (600) defines a ring or circle. It should be noted, however, that the perimeter of the support structure (600) can define any polygonal shape, including circles, without departing from the scope and spirit of the present invention. Further, preferably, the shape defined by the protective outer barrier (300) will be similar to the shape defined by the outer perimeter of the floating support structure (600) since the protective outer barrier structure (300) encompasses the aquatic area defined by the outer perimeter of the floating support structure (600). As depicted in FIG. 1b, the outer perimeter of floating support structure (600) defines a circle and the protective outer barrier (300) defines a ring. That said, it will be appreciated by one of ordinary skill in the art that the shape defined by protective outer barrier (300) may be different from that defined by the outer perimeter of support structure (600) without departing from the scope and spirit of the present invention.

Figure 3:
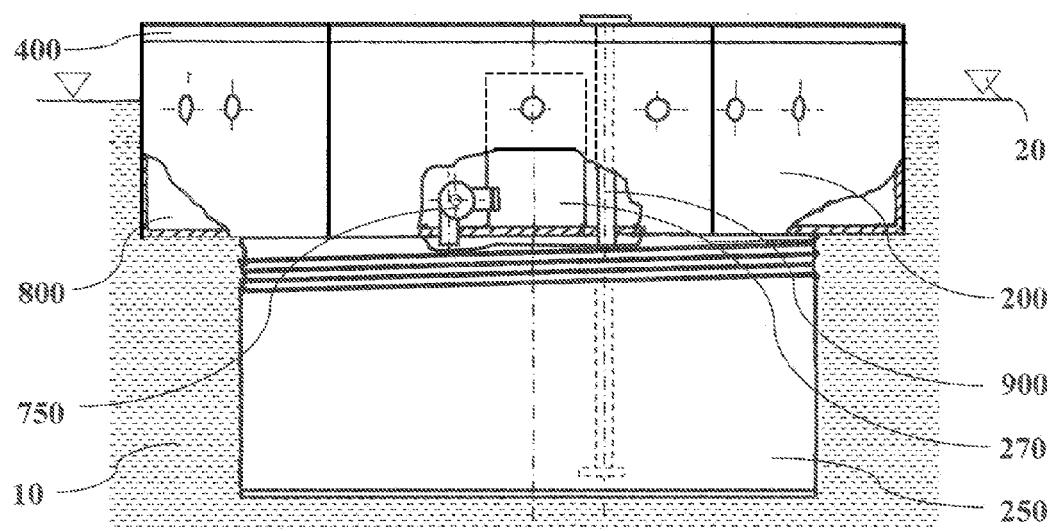
FIG. 3 is an elevation view with a partial cross section of one embodiment of the apparatus' microalgae processing and control assembly shown floating partially submerged.

As best seen in FIG. 1a and FIG. 3, some embodiments of the microalgae production support system (30) further comprise a submerged, expendable microalgae storage tank (250) mechanically associated to and in hydraulic communication with the microalgae processing and control assembly (200). Storage tank (250) is configured to store the harvested microalgae until retrieved by a support vehicle or similar system. For some embodiments, storage tank (250) defines a variable volume storage tank using any suitable technology such as telescopic arrangements, collapsible sides (similar to flexible drinking straws), twisting thread and grove type arrangements, and the use of somewhat elastic materials that stretch under load.

FIG. 1b further depict a main photovoltaic panel assembly (400) positioned above and electrically associated with the microalgae processing and control assembly (200). The main photovoltaic panel assembly (400) is configured for providing the electrical energy required to operate the apparatus during the day. Such systems are well known by those of ordinary skill in the art; consequently, a detailed description of the photovoltaic system is unnecessary.

FIG. 1b further depict a plurality of photovoltaic subassemblies (500) positioned on the protective outer barrier structure (300) and electrically associated with the microalgae processing and control assembly (200). The plurality of photovoltaic subassemblies (500) is configured to generate and store the electrical energy required to operate the apparatus during the night. Such systems are well known by those of ordinary skill in the art; consequently, a detailed description of the photovoltaic system is unnecessary.

Motion Facilitator

FIG. 1a further depicts the preferred embodiment comprising a vertically extending mast assembly (350) defining a top end and an opposing bottom end. The bottom end of mast assembly (350) is mechanically associated with the microalgae processing and control assembly (200). The top end of mast assembly (350) is mechanically associated with anchor subassembly (360). For the presently preferred embodiment, anchor subassembly (360) comprises a plurality of stabilizing members configured to enhance the system's structural stability. For the preferred embodiment, the first ends of said plurality of stabilizing members are mechanically associated with the top end of mast assembly (350). The opposing second ends of said plurality of stabilizing members are mechanically associated, radially (i.e. equally spaced), with protective outer barrier structure (300). The number of stabilizing members is preferably selected so that the tension of one stabilizing member is offset by at least one other stabilizing member. For the preferred embodiment depicted in FIG. 1a, there are six stabilizing members defining three opposing stabilizing member pairs. Alternatively, a stabilizing member could span the entire protective outer barrier structure (300) where the center of such stabilizing member is mechanically associated with the top end of mast assembly (350) with the two ends mechanically associated with protective outer barrier structure (300). One of ordinary skill in the art will appreciated that such a configuration helps mechanically associate the outer barrier (300) with the microalgae processing and control assembly (200) while also providing enhanced stability and support for mast assembly (350). Furthermore, FIG. 1a depicts the mast assembly (350) providing deployment for antennas, satellite dishes and other electronic and visual identification means (370).

Figure 4:
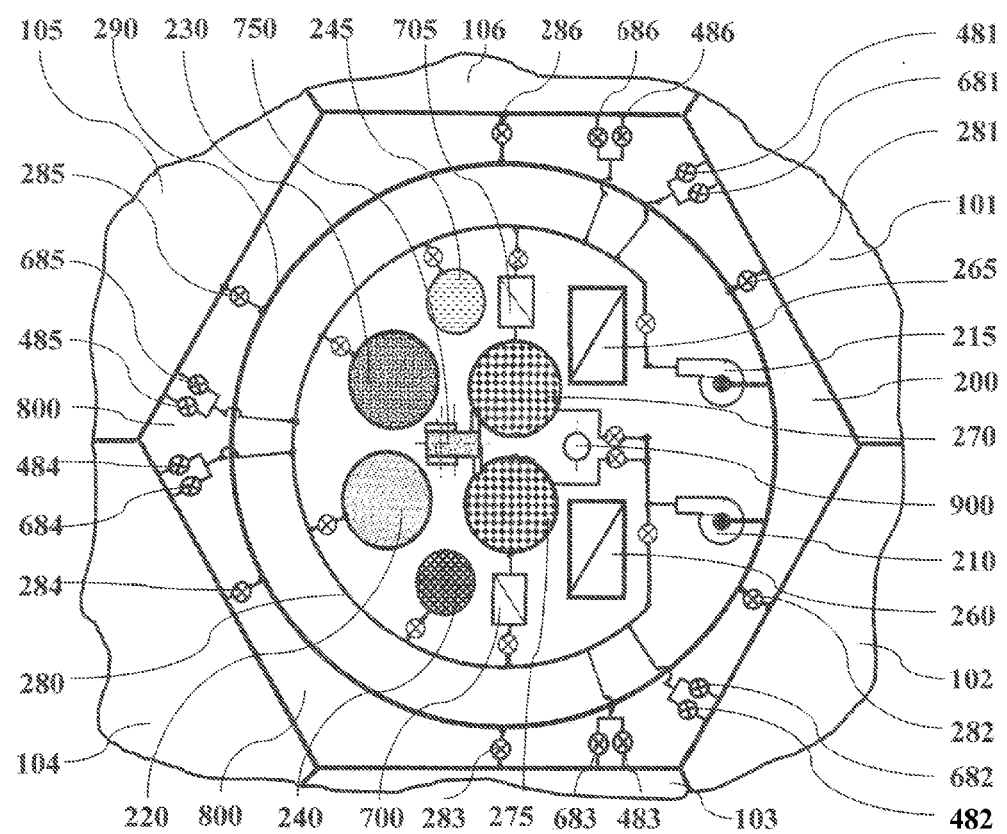
FIG. 4 is a hydraulic diagram of the apparatus' microalgae processing and operational control positioned inside the water-sealed chamber assembly (800).

Referring now to FIG. 4 of the currently preferred embodiment of the microalgae production apparatus, a motion facilitator controller (265) is shown inside a water-sealed chamber assembly (800) that is integral part of microalgae processing and control assembly (200). The motion facilitator controller (265) is configured to use the antennas, satellite dishes and other electronic and visual identification means (370) located on the mast assembly (350) to determine and communicate the apparatus' deployment coordinates and initiate migration either automatically and/or on demand (via signals received from an external device) using a plurality of swivel propellers (330) mechanically associated with the bottom of the protective outer barrier structure. One of ordinary skill in the art will appreciate that the motion facilitator controller could command any number of suitable devices configured to maneuver the microalgae production apparatus in the aquatic environment without departing from the scope and spirit of the invention including water-jet based propulsion systems.

Microalgae Producing System

Figure 2:
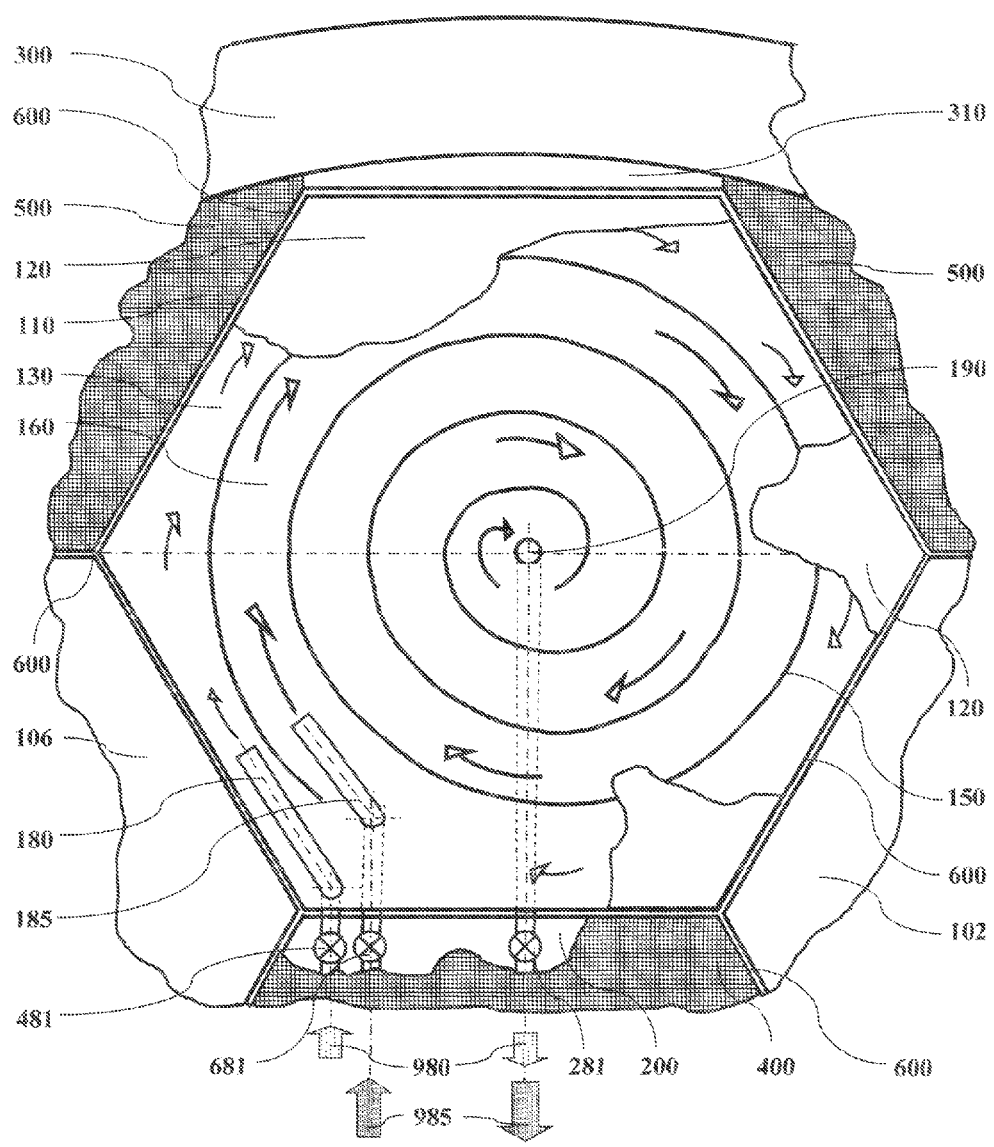
FIG. 2 is a partial top view of the preferred embodiment with a partial cross section of the apparatus's photo-bioreactor (101) as shown in FIG. 1b.

As best seen in FIG. 1b and FIG. 2, the currently preferred embodiment of microalgae producing system (40) comprises a plurality of flatbed, gas permeable, photo-bioreactors. Such photo-bioreactors are arranged in a cluster of six identical photo-bioreactors: (101), (102), (103), (104), (105), and (106) (or simply 101-106) deployed around a centrally positioned microalgae processing and control assembly (200); all being encompassed by a protective outer barrier (300). A floating honeycomb-shaped assembly (600) connects the protective outer barrier (300) with the microalgae processing and control assembly (200). The floating support structure (600) defines deployment areas configured to provide structural support for the photo-bioreactors deployed in the cluster. FIG. 1b also shows six identical photovoltaic subassemblies (500) positioned on the floating support structure (600) and mechanically associated with the protective outer barrier structure (300) to provide additional power to the apparatus' electrical and energy storage devices and systems. As stated above, a main photovoltaic panel (400) is mechanically associated with the microalgae processing and control assembly (200).

FIG. 2 shows one of the apparatus's six identical photo-bioreactors, namely the photo-bioreactor 101, disposed inside a deployment area defined by floating support structure (600). As described above, floating support structure (600) is preferably mechanically associated to the microalgae processing and control assembly (200). Similarly, floating support structure (600) is mechanically associated with the protective outer barrier (300) via a connector subassembly (310).

FIG. 2 also shows the flatbed photo-bioreactor (101) disposed in a deployment area adjacent to the photo-bioreactors (102) and (106) as well as microalgae processing and control assembly (200). As depicted in the cut away section of FIG. 2, flatbed photo-bioreactor (101) is in hydraulic communication with the microalgae processing and control assembly (200) through intake valves (481) and (681), and a return valve (281). Each photo-bioreactor defines a similar hydraulic communication configuration with the microalgae processing and control assembly (200). The flatbed photo-bioreactor (101) further comprises an upper hexagonal shaped light transparent and $CO_2/O_2$ gas-permeable top membrane assembly (120) mechanically associated with a lower $CO_2/O_2$ gas-permeable bottom membrane assembly (130) by sidewall assembly (110). It will be appreciated by one of ordinary skill in the art that the photo-bioreactors and associated membrane assemblies may define any polygonal shape (including circles) without departing from the scope and spirit of the invention.

For the currently preferred embodiment, flatbed photo-bioreactor (101) further comprises a spiral-shaped wall assembly (150) disposed between the top membrane assembly (120) and the bottom membrane assembly (130). Preferably, such spiral-shaped wall assembly (150) is sealed to both the top membrane assembly (120) and the bottom membrane assembly (130). The spiral-shaped wall assembly (150) is configured to control the flow of substances inside the flatbed photo-bioreactor thereby helping to define the boundaries between different zones within the flatbed photo-bioreactor (101). More specifically, a microalgae-harvesting zone (160) is defined by spiral-shaped wall assembly (150). For the currently preferred configuration, the microalgae-harvesting zone (160) is the volume within flatbed photo-bioreactor (101) having two boundaries defined by wall assembly (150) and one boundary defined by the top membrane assembly (120) and one boundary defined by the bottom membrane assembly (130). A low-speed water-algae-nutrients mixture return inlet (180) is disposed outside the microalgae-harvesting zone (160) while a high-speed water-nutrients mixture return inlet (185) is disposed at least partially inside the microalgae-harvesting zone (160). Substances exit the flatbed photo-bioreactor (101) through outlet (190) which is hydraulically associated with the microalgae processing and control assembly (200) through return valve (281). Each flatbed photo-bioreactor defines a similar configuration.

Each flatbed photo-bioreactor (101-106) defines at least two modes of operation. As depicted in FIG. 2, intake valve (481) is disposed in the microalgae processing and control assembly (200) and is hydraulically associated with low-speed water-algae-nutrients mixture return inlet (180) disposed in photo-bioreactor (101). Activating intake valve (481) enables the photo-bioreactor (101) microalgae-growth mode of operation illustrated by the low-speed flow directional arrows (980). Similarly, intake valve (681) is disposed in the microalgae processing and control assembly (200) and is hydraulically associated with high-speed water-nutrients mixture return inlet (185) disposed in photo-bioreactor (101). Activating intake valve (681) enables the microalgae-harvesting mode of operation illustrated by the high-speed flow directional arrows (985). Furthermore, FIG. 2 shows an return valve (281), disposed in the microalgae processing and control assembly (200), hydraulically associated with outlet (190) which is hydraulically associated with both mixture return inlet (180) and mixture return inlet (185). Notably, return valve (281) remains open when Photo-bioreactor (101) is selected for microalgae-growth or microalgae-harvesting mode of operation. Thus, one of ordinary skill in the art will appreciate that such a configuration defines a closed loop system between each flatbed photo-bioreactor (101-106) and the microalgae processing and control assembly (200).

It will be appreciated that inlet valves (180) and (185) and return valves (281) may be disposed in systems other than the microalgae production and support system (30) without departing from the scope and spirit of the present invention. For example, such valves could be disposed in, or associated with, the flatbed photo-bioreactor (101-106) and then hydraulically associated with the microalgae production and support system (30) via ports.

Referring now to FIG. 3, a microalgae processing and control assembly (200) comprising an internal water-sealed chamber assembly (800) coupled to microalgae storage tank (250) in a watertight configuration is considered. Water-sealed chamber assembly (800) comprises a mud-pump assembly (750) configured to transfer harvested microalgae from the centrifugal separators (270) and (275) (not shown) into the submerged microalgae storage tank (250). Water-sealed chamber assembly (800) further comprises a hollow vertical shaft assembly (900) configured to provide a transfer path from the microalgae storage tank (250) to a receiver (such as support ship) wherein such transfer path is suitable for facilitating the transfer of the contents of storage tank (250).

FIG. 4 shows the water-sealed chamber assembly (800) further comprising an algae production control subassembly (260) configured to control the operational mode for each of the apparatus' photo-bioreactors. Such operational modes include the microalgae-growth mode and the microalgae-harvesting mode.

Water-sealed chamber assembly (800) comprises an intake manifold (290) and a pressurized return manifold (280). As depicted in FIG. 4, intake manifold (290) is hydraulically associated with outlet valves (281-286). Similarly, pressurized return manifold (280) is hydraulically associated with inlet valves (481-486) and inlet valves (681-686) thereby placing such manifolds in hydraulic communication with the cluster of photo-bioreactors.

FIG. 4 further shows the water-sealed chamber assembly (800) comprising a low-pressure pump (215) in hydraulic communication with return manifold (280). Low-pressure pump (215) is used by algae production control subassembly (260) when operating in microalgae-growth mode, to recirculate a water-algae-nutrients mixture inside a selected photo-bioreactor at a flow rate that results in minimal or no damage to the micro-algae's biological integrity. Furthermore, nutrients dispensers (220) and (230), via their back-flow protection valves, are hydraulically associated with return manifold (280) and are configured to dispense substances (such as nutrients) into the return manifold (280) upon request from the algae production control subassembly (260). Similarly, a water dispenser (240) and an algae culture dispenser (250), via back-flow protection valves, are hydraulically associated with return manifold (280) and are configured to dispense substances (such as water and algae culture) into the return manifold upon receiving a request from the algae production control subassembly (260).

FIG. 4 shows the water-sealed chamber assembly (800) further comprising a high-speed, high-flow pump (210) in hydraulic communication with return manifold (280). High-flow pump (210) is selected by the algae production control subassembly (260) to operate a selected photo-bioreactor in microalgae harvesting mode by pumping a water-algae-nutrients mixture from a selected photo-bioreactor in hydraulic communication with the intake manifold (290) into centrifugal separators (270) and (275), and, using filtering units (700) and (705), to return a substantially algae free water-nutrients mixture to the pressurized return manifold (280). Furthermore, FIG. 4 shows a mud-pump assembly (750) configured for transferring the harvested microalgae from the centrifugal separators (270) and (275) into microalgae storage tank (250) (not shown in FIG. 4).

As best seen in FIG. 4, intake manifold (290) and return manifold (280) are configured to be cyclically connected, on request from the algae production control subassembly (260), to one of the photo-bioreactors 101, 102, 103, 104, 105, and 106 by enabling the intake valves (481-486) and the return valves (281-286) when operating in the microalgae-growth mode, or enabling the intake valves (681-686) and the return valves (281-286) when operating in the microalgae harvesting mode.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

What is claimed is:

1. A continuous-microalgae-production apparatus operating in an aquatic field comprising:
   a microalgae production-support system suitably configured to support continuous-microalgae-production in said aquatic field, said microalgae production-support system comprising:
   (a) a floatable, waves-protective, outer-barrier structure suitably configured to surround said continuous-microalgae-production apparatus, and wherein said outer-barrier structure defines an inner perimeter and an outer perimeter, and wherein said inner perimeter defines an aquatic area, and wherein said outer-barrier structure is suitably configured to provide waves protection for said aquatic area; and
   (b) a floatable, microalgae processing-and-control assembly deployed inside said aquatic area, wherein said floatable microalgae processing-and-control assembly further comprises a submerged microalgae-storage tank mechanically associated with and in hydraulic communication with said floatable microalgae processing-and-control assembly; and
   a continuous-microalgae-production system comprising:
   (a) at least one continuous-production, dual-zone, photo-bioreactor configured to operate underwater independent of atmospheric, land-based, or ship-based supplied carbon dioxide gas, and wherein said at least one continuous-production, dual-zone, photo-bioreactor is suitably configured to allow the carbon dioxide dissolved in the surrounding waters to enter said at least one continuous-production, dual-zone, photo-bioreactor, and wherein said at least one continuous-production, dual-zone, photo-bioreactor defines the shape of a shallow-box container comprising an upper surface and a lower surface separated by a plurality of side surfaces thereby defining an internal volume and wherein at least part of said upper surface defines a underwater-gas-permeable top-membrane assembly and a light-transparent top-membrane sub-assembly, and wherein at least part of said lower surface defines a underwater-gas-permeable bottom-membrane assembly; and
   (b) a floatable, support-structure deployed inside said aquatic area at least partly adjacent to said microalgae-processing-and-control assembly and at least partly below said at least one continuous-production, dual-zone, photo-bioreactor, wherein said support-structure is suitably configured to partition at least part of said aquatic area into at least one photo-bioreactor-deployment area suitably configured to keep submerged in the proximity of the water surface said at least one continuous-production, dual-zone, photo-bioreactor, and wherein said floatable support-structure is mechanically associated with both of said waves-protective outer-barrier structure and said microalgae-processing-and-control assembly.

2. A continuous-microalgae-production apparatus operating in an aquatic field as in claim 1, wherein:
   said plurality of side surfaces define a sidewall assembly following the perimeter of said at least one continuous-production, dual-zone, photo-bioreactor;
   said at least one continuous-production, dual-zone, photo-bioreactor is deployed in said aquatic-area so that said sidewall assembly substantially follows the perimeter defined by said at least one photo-bioreactor-deployment area;

said sidewall assembly has a constant structural height of about four inches;

said sidewall assembly defines a surface area that is smaller than the surface area defined by either of said upper surface and said lower surface and the surface area of said upper surface is substantially equal to the surface area of said lower surface; and wherein said sidewall assembly mechanically associates said upper surface to the said lower surface thereby defining said internal volume for said continuous-production, dual-zone, photo-bioreactor.

3. A continuous-microalgae-production apparatus operating in an aquatic field as in claim 1, wherein said plurality of side surfaces define a sidewall assembly following the perimeter of said at least one continuous-production, dual-zone, photo-bioreactor and wherein said internal volume further comprises a spiral-shaped wall assembly disposed inside said internal volume, and wherein said spiral-shaped wall assembly defines a constant structural height equal to the structural height of said sidewall assembly, and wherein said spiral-shape wall assembly mechanically connects said upper surface to said lower surface.

4. A continuous-microalgae-production apparatus operating in an aquatic field as in claim 3, wherein said spiral-shaped wall assembly defines a microalgae-harvesting zone and a microalgae-continuous-presence zone wherein said microalgae-harvesting zone is centrally positioned inside said internal volume, and wherein said microalgae-continuous-presence zone is positioned outside said microalgae-harvesting zone, and wherein said microalgae-harvesting zone and said microalgae-continuous-presence zone equally divide said internal volume and provide for continuous-production of microalgae inside said at least one continuous-production, dual-zone, photo-bioreactor.

5. A continuous-microalgae-production apparatus operating in an aquatic field as in claim 4, wherein said at least one continuous-production, dual-zone, photo-bioreactor further comprises a first-return-inlet located inside said microalgae-continuous-presence zone, and wherein said first-return-inlet is in hydraulic communication with said microalgae-processing-and-control assembly, and wherein said first-return-inlet is used to recirculate a water-algae-nutrients mixture inside said at least one continuous-production, dual-zone, photo-bioreactor when said photo-bioreactor is operating in a microalgae-growth mode.

6. A continuous-microalgae-production apparatus operating in an aquatic field as in claim 4, wherein said at least one continuous-production, dual-zone, photo-bioreactor further comprises a second-return-inlet located inside said microalgae-harvesting zone, and wherein said second-return-inlet is in hydraulic communication with said microalgae-processing-and-control assembly, and wherein said second-return-inlet is used to return a water-nutrients mixture to a said at least one continuous-production, dual-zone, photo-bioreactor when said photo-bioreactor is operating in a microalgae-harvesting mode.

7. A continuous-microalgae-production apparatus operating in an aquatic field as in claim 4, wherein said at least one continuous-production, dual-zone, photo-bioreactor comprises a hydraulic-outlet suitably configured to operate during both said microalgae-growth mode and said microalgae-harvesting mode of operation, wherein said hydraulic outlet is located inside said microalgae-harvesting zone, and wherein said hydraulic outlet is in hydraulic communication with said microalgae-processing-and-control assembly.

8. A continuous-microalgae-production apparatus operating in an aquatic field as in claim 1, wherein said microalgae-processing-and-control assembly is water-sealed and further comprises a main photovoltaic panel assembly suitably configured to provide electrical energy independent of land or ship supplied energy sources and wherein said main photovoltaic panel assembly is suitably configured to provide the electrical energy required to operate said microalgae-processing-and-control assembly during the day.

9. A continuous-microalgae-production apparatus operating in an aquatic field as in claim 1, wherein said microalgae-processing-and-control assembly is suitably configured to store the renewable energy provided by a plurality of photovoltaic subassemblies, wherein said plurality of photovoltaic subassemblies are at least one of mechanically and electrically associated with at least one of (a) said waves-protective outer-barrier structure and (b) said microalgae-processing-and-control assembly, and wherein said plurality of photovoltaic subassemblies are suitably configured to store the electrical energy required to operate said microalgae-processing-and-control assembly during the night.

10. A continuous-microalgae-production apparatus operating in an aquatic field as in claim 1, wherein said microalgae-processing-and-control assembly further comprises a communication-controller suitably configured to determine the continuous-microalgae-production apparatus' deployment coordinates and operational status in response to a remote request and wherein said microalgae-processing-and-control assembly further comprises a microalgae-production-controller suitably configured to automatically select a said mode of operation for said at least one continuous-production, dual-zone, photo-bioreactor.

11. A continuous-microalgae-production apparatus operating in an aquatic field as in claim 1, further comprising six substantially identical hexagonal-shaped, continuous-production, dual-zone photo-bioreactors and wherein said floatable support-structure defines six substantially identical hexagonal-shaped photo-bioreactor-deployment areas positioned adjacent and surrounding said microalgae-processing-and-control assembly, and wherein said six hexagonal-shaped photo-bioreactor-deployment areas are suitably configured to keep submerged in the proximity of the water surface and inside the perimeter defined by each one of the said six hexagonal-shaped photo-bioreactor-deployment areas, said six substantially identical hexagonal-shaped, continuous-production, dual-zone photo-bioreactors, and wherein each of said hexagonal-shaped, continuous-production, dual-zone, photo-bioreactor are in hydraulic communication with said microalgae-processing-and-control assembly and wherein said microalgae-storage tank defines a variable volume tank.

12. A continuous-microalgae-production apparatus operating in an aquatic field comprising:

a outer-barrier structure defining an inner perimeter and an outer perimeter wherein said inner perimeter defines an aquatic area;

a floatable support-structure disposed in said aquatic area wherein said support-structure partitions at least part of said aquatic area into at least one photo-bioreactor-deployment area;

a microalgae processing-and-control assembly deployed inside said aquatic area and outside said at least one photo-bioreactor-deployment area wherein said microalgae processing-and-control assembly comprises a submerged microalgae-storage tank mechanically associated with and in hydraulic communication with said microalgae processing-and-control assembly and wherein said microalgae processing-and-control assembly is mechanically associated with said support-structure;

a continuous-microalgae-production system comprising at least one continuous-production, dual-zone, photo-bioreactor disposed submerged in said at least one photo-bioreactor-deployment area;

wherein said at least one continuous-production, dual-zone, photo-bioreactor defines the dimensional characteristics of an enclosed shallow-box container having an upper surface with a surface area of at least 100 square yards and an opposing lower surface with a surface area of at least 100 square yards, wherein said upper surface and said lower surface are separated by a sidewall assembly defining a height of about four inches thereby defining an internal-bioreactor-volume;

wherein said at least one photo-bioreactor-deployment area is suitably configured to keep said at least one continuous-production, dual-zone, photo-bioreactor submerged in the proximity of the water surface at a depth suitable for underwater-light-penetration into said at least one continuous-production, dual-zone, photo-bioreactor;

wherein said lower surface is configured with a bottom-membrane assembly defining an underwater-gas-permeable membrane and wherein said upper surface is configured with an top-membrane assembly defining an underwater-gas-permeable membrane and wherein said underwater-gas-permeable membranes are configured to allow the indigenous carbon dioxide dissolved in the water surrounding said at least one continuous-production, dual-zone, photo-bioreactor to enter said photo-bioreactor for said photo-bioreactor's photosynthesis related processes; and wherein said support-structure is mechanically associated with said microalgae-processing-and-control assembly.

13. A continuous-microalgae-production apparatus operating in an aquatic field as in claim 12, wherein:

said underwater-gas-permeable top-membrane assembly further defines a light-transparent membrane;

at least part of the outer perimeter of said support-structure is mechanically associated with said outer-barrier structure configured;

said outer-barrier structure is configured to provide waves protection for said aquatic area; and said microalgae processing-and-control assembly defines a water-sealed assembly and said microalgae-storage tank defines a variable volume tank.

14. A continuous-microalgae-production apparatus operating in an aquatic field as in claim 12, further comprising a spiral-shaped wall assembly disposed inside said internal-bioreactor-volume, and wherein said spiral-shaped wall assembly has a constant structural height equal to the structural height of said sidewall assembly, and wherein said spiral-shape wall assembly mechanically connects said upper surface to said lower surface.

15. A continuous-microalgae-production apparatus operating in an aquatic field as in claim 14, wherein said spiral-shaped wall assembly is suitably configured to provide for continuous-production of microalgae inside said continuous-production, dual-zone, photo-bioreactor, by defining a microalgae-harvesting zone inside said internal-bioreactor-volume, and wherein said spiral-shaped wall assembly further defines a microalgae-continuous-presence zone positioned inside said internal-bioreactor-volume and outside said microalgae-harvesting zone.

16. A continuous-microalgae-production apparatus operating in an aquatic field as in claim 15, wherein said microalgae-harvesting zone is centrally positioned inside said internal-bioreactor-volume and wherein said microalgae-harvesting zone is substantially equal in size to said microalgae-continuous-presence zone.

17. A continuous-microalgae-production apparatus operating in an aquatic field as in claim 16, wherein said continuous-production, dual-zone, photo-bioreactor further comprises a first-return-inlet located inside said microalgae-continuous-presence zone, and wherein said first-return-inlet is in hydraulic communication with said microalgae-processing-and-control assembly, and wherein said first-return-inlet is used to recirculate a water-algae-nutrients mixture inside said at least one continuous-production, dual-zone, photo-bioreactor when said photo-bioreactor is operating in a microalgae-growth mode; and wherein said continuous-production, dual-zone, photo-bioreactor further comprises a second-return-inlet located inside said microalgae-harvesting zone, and wherein said second-return-inlet is in hydraulic communication with said microalgae-processing-and-control assembly, and wherein said second-return-inlet is used to return a water-nutrients mixture to a said at least one continuous-production, dual-zone, photo-bioreactor when said photo-bioreactor is operating in a microalgae-harvesting mode.

18. A continuous-microalgae-production apparatus operating in an aquatic field as in claim 17, wherein said microalgae-processing-and-control assembly further comprises a controller suitably configured to determine the deployment coordinates and operational status information of said continuous-microalgae-production apparatus and transmit said coordinates and said operational status information to a remote device and wherein said controller is further configured to automatically select a mode of operation for said at least one continuous-production, dual-zone, photo-bioreactor thereby defining a substantially autonomic system operating without the need for continuous manual intervention.

19. A method of continuously producing microalgae in an aquatic field without a continuous manual presence, said method comprising the steps of:

deploying a selectively buoyant outer-barrier structure in an aquatic field wherein said outer-barrier structure defines an inner perimeter and an outer perimeter, and wherein said inner perimeter defines an aquatic-area, and wherein said outer-barrier structure is suitably configured to provide waves protection for said aquatic-area;

deploying a selectively buoyant microalgae processing-and-control assembly in the approximate center of said aquatic-area wherein said microalgae processing-and-control assembly comprises a submerged microalgae-storage tank mechanically associated with and in hydraulic communication with said microalgae processing-and-control assembly;

deploying a selectively buoyant support-structure in said aquatic-area wherein said support-structure defines an outer perimeter and an inner perimeter and wherein said support-structure at least partially surrounds said microalgae processing-and-control assembly and partitions at least part of said aquatic-area into at least one photo-bioreactor-deployment area and wherein at least part of said outer perimeter is mechanically associated with said outer-barrier structure;

mechanically associating said support-structure with said microalgae-processing-and-control assembly;

deploying a continuous-microalgae-production system inside said aquatic-area wherein said continuous-microalgae-production system comprises at least one continuous-production photo-bioreactor disposed submerged in said at least one photo-bioreactor-deployment area and supported by said support-structure at a depth suitable for underwater-light-penetration into said at least one continuous-production photo-bioreactor;

wherein said at least one continuous-production photo-bioreactor has the dimensional characteristics of an enclosed shallow-box container comprising a substantially flat top section and an opposing substantially flat bottom section connected along their perimeters by a sidewall assembly defining a container depth of about four inches and thereby defining an internal-bioreactor-volume;

configuring said bottom section with a bottom-membrane assembly defining an underwater-gas-permeable membrane;

configuring said top section with an top-membrane assembly defining an underwater-gas-permeable and light-transparent membrane;

configuring said underwater-gas-permeable membranes to allow the indigenous carbon dioxide dissolved in the water surrounding said at least one continuous-production, photo-bioreactor to enter said photo-bioreactor for said photo-bioreactor's photosynthesis related processes and wherein the surface area of said top section and the surface area of said bottom section is larger than the surface area of said sidewall assembly making the introduction of non-indigenous carbon dioxide into said internal-bioreactor-volume or surrounding water unnecessary for said photo-bioreactor's photosynthesis related processes;

providing a spiral-shaped wall assembly disposed inside said internal-bioreactor-volume wherein said spiral-shaped wall assembly has a constant structural height equal to the structural height of said sidewall assembly, and wherein said spiral-shape wall assembly mechanically connects said top-membrane assembly to the said bottom-membrane assembly;

configuring said spiral-shaped wall assembly to divide said internal-bioreactor-volume into a microalgae-harvesting zone and a microalgae-continuous-presence;

deploying a first-return-inlet disposed inside said microalgae-continuous-presence zone wherein said first-return-inlet is in hydraulic communication with said microalgae-processing-and-control assembly;

configuring said first-return-inlet to recirculate a water-algae-nutrients mixture inside said at least one continuous-production, photo-bioreactor when said photo-bioreactor is operating in a microalgae-growth mode;

deploying a second-return-inlet located inside said microalgae-harvesting zone wherein said second-return-inlet is in hydraulic communication with said microalgae-processing-and-control assembly;

configuring said second-return-inlet to return a water-nutrients mixture to said at least one continuous-production, photo-bioreactor when said photo-bioreactor is operating in a microalgae-harvesting mode;

providing a controller suitably configured to automatically select a mode of operation for said at least one continuous-production, photo-bioreactor; and configuring said controller to determine the deployment coordinate information and monitor the operational status information for said at least one continuous-production, photo-bioreactor and to transmit a data-signal containing at least part of, and at least one of, said deployment coordinate information and operational status information to a remote device.

20. A method of continuously producing microalgae in an aquatic field as in claim 19, further comprising the steps:

configuring the outer perimeter of said microalgae processing-and-control assembly to define a hexagonal shape and centrally deploying said microalgae processing-and-control assembly inside said aquatic-area;

configuring said a support-structure to surround said microalgae processing-and-control assembly thereby partitioning the aquatic-area surrounding said microalgae processing-and-control assembly into at least one photo-bioreactor-deployment area;

deploying six equally sized hexagonal shaped continuous-production photo-bioreactors disposed submerged in said at least one photo-bioreactor-deployment area wherein each of said six equally sized hexagonal shaped continuous-production photo-bioreactors are supported by said support-structure at a depth suitable for underwater-light-penetration into each of said six equally sized hexagonal shaped continuous-production photo-bioreactors;

placing each of six equally sized hexagonal shaped continuous-production photo-bioreactors in hydraulic communication with said microalgae processing-and-control assembly;

configuring said storage-tank with a variable volume structure; and configuring the spiral-shaped wall assembly inside each of said six equally sized hexagonal shaped continuous-production photo-bioreactors to centrally position said microalgae-harvesting zone inside its respective internal-bioreactor-volume.

* * * * *